(12) United States Patent
Newman et al.

(10) Patent No.: US 6,942,977 B1
(45) Date of Patent: Sep. 13, 2005

(54) IMMUNOASSAYS FOR DETERMINING VITAMIN B12, AND REAGENTS AND KITS THEREFOR

(75) Inventors: Karel Newman, Eden Prairie, MN (US); Jane Schmidt, St. Paul, MN (US); Paul Wegfahrt, Downingtown, PA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 08/070,099

(22) Filed: May 28, 1993

Related U.S. Application Data

(63) Continuation-in-part of application No. 07/682,060, filed on Apr. 9, 1991, now abandoned.

(51) Int. Cl.$^7$ .................. C07K 16/28; C07K 16/18; G01N 33/53; G01N 33/58
(52) U.S. Cl. ................ 435/7.1; 530/387.1; 530/387.9; 530/388.1; 530/388.24; 530/388.25; 436/501; 436/63; 435/7.2; 435/7.21; 435/7.9; 435/345
(58) Field of Search ................... 435/7.9, 7.1, 7.2, 435/7.21, 345; 530/388.24, 387.1, 387.9, 530/388.1, 388.25; 424/85.9; 436/501, 63

(56) References Cited

U.S. PATENT DOCUMENTS

| | | | |
|---|---|---|---|
| 3,505,019 A | 4/1970 | Axen et al. | 23/230 |
| 4,188,189 A | 2/1980 | Allen | 23/230 |
| 4,333,918 A | 6/1982 | Carney et al. | 424/1 |
| 4,351,822 A | 9/1982 | Allen | 424/1 |
| 4,355,018 A | 10/1982 | Hansen et al. | 424/1 |
| 4,418,151 A | 11/1983 | Forand et al. | 436/525 |
| 4,423,154 A | 12/1983 | Gutcho et al. | 436/505 |
| 4,426,455 A | 1/1984 | Tovey et al. | 436/505 |
| 4,447,528 A | 5/1984 | Ellis et al. | 435/7 |
| 4,451,571 A | 5/1984 | Allen | 436/505 |
| 4,465,775 A | 8/1984 | Houts | 436/503 |
| 5,310,656 A * | 5/1994 | Pourfarzaneh et al. | 435/7.93 |

FOREIGN PATENT DOCUMENTS

| | | | |
|---|---|---|---|
| WO | 9100519 | 1/1991 | C07K 15/28 |

OTHER PUBLICATIONS

Roitl et al., *Essential Immunology*, Goner Medical Publ. 34-42 Cleveland St, London WIP5FB. pp. 7.1-7.6, 1989.*
Samoloff, I. M. et al. Journal of Immunology, 101(3): 578-586, 1968.*
W. Pfund, et al., The Conformation-Sensitive Immunoassay: A Membrane Based Elisa System for Identifying Antibodies Sensitive to Alteration of Protein Conformation: *Molecular Immunology*, 27:495-502 (1990).
J. Kolhouse, et al., "Cobalamin Analogues are Present in Human Plasr and Can Mask Cobalamin Deficiency Because Current RadioisotopeDilution Assays Are Not Specific For Tru Cobalamin, " *The New England Journal of Medicine*, 299:785-792 (1970).
G. Garrido-Pinson, et al., "Studies of Human Intrinsic Factor Auto-Antibodies, " *Journal of Immunology*, 97:897-912 (1966).
K. Taylor, "Inhibition of Intrinsic Factor by Pernicious Anaemia Sera, " *The Lancet*, 2:106-108 (1959).
M. Schwartz, "Intrinsic Factor Antibody in Serum From Patients With Pernicious Anemia, " *The Lancet*, 2:1263-1267 (1960).
I. Chen, et al., "Clinical Significance of Serum Vitamin B12 Measured by Radioassay Using Pure Intrinsic Factor, " *Clinical Sciences: Journal of Nuclear Medicine*, 22:447-451 (1981).
Smokla, et al., *Gastroenterology*, 98:607-614 (1990).
Galfre, et al., *Methods of Enzymology*, 73:3-46 (1981).

* cited by examiner

*Primary Examiner*—Alana M. Harris
*Assistant Examiner*—Anne L. Holleran
(74) *Attorney, Agent, or Firm*—Townsend and Townsend and Crew LLP

(57) ABSTRACT

Methods are described for the development of monoclonal antibodies to intrinsic factor and the application of said antibodies in the development of B12 immunoassays. In particular, antibodies are described that are capable of binding to intrinsic factor only in the absence of vitamin B12, and that are released from binding in the presence, and upon the binding, of vitamin B12 to intrinsic factor. Assays may be formatted such that either antibody or intrinsic factor is immobilized or labeled.

9 Claims, 1 Drawing Sheet

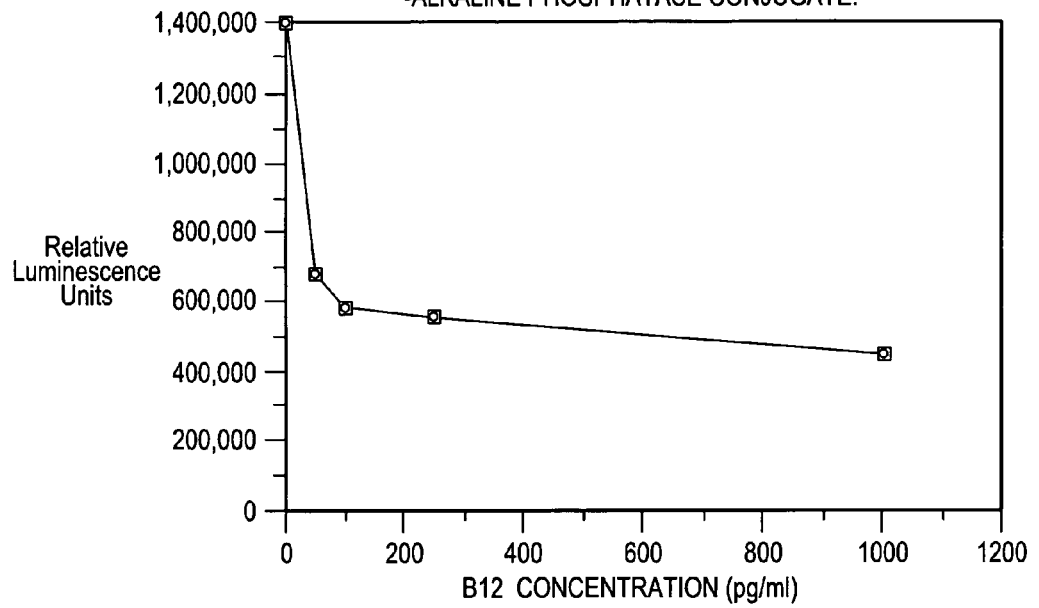
FIG. 1 B12 IMMUNOASSAY STANDARD CURVE
CLONE 585.3A3A8 PAIRED WITH INTRINSIC FACTOR -ALKALINE PHOSPHATASE CONJUGATE.
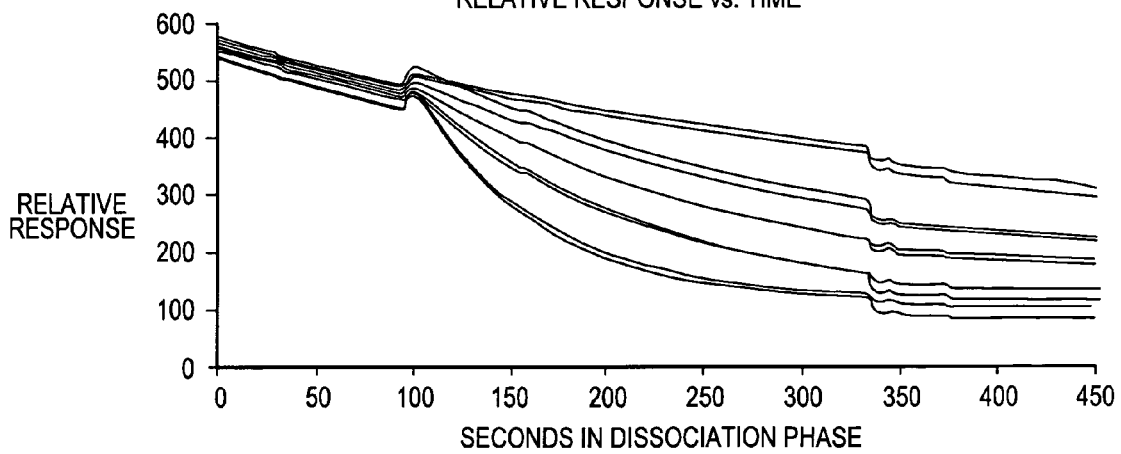
FIG. 2 RELATIVE RESPONSE vs. TIME

IMMUNOASSAYS FOR DETERMINING VITAMIN B12, AND REAGENTS AND KITS THEREFOR

This application is a continuation-in-part of U.S. application Ser. No. 07/682,060, filed Apr. 9, 1991, now abandoned.

FIELD OF THE INVENTION

The present invention relates to immunoassays for determining vitamin B12 levels in a sample, and particularly to immunoassays utilizing anti-intrinsic factor antibodies.

BACKGROUND OF THE INVENTION

Assays to determine vitamin B12 levels in humans have long been recognized as a valuable tool in the diagnosis and treatment of such diseases as pernicious anaemia. Vitamin B12 is required for the maintenance of homeostasis.

Vitamin B12 was first purified in 1948. Its complete molecular structure was subsequently elucidated. It has an organometallic corrin nucleus with a stabilized central cobalt ion. The biological activity of such corrin compounds is determined by the composition of the side chain, of which only molecules possessing an "A" ring conjugated nucleotide alpha-ribazole side chain stabilizing the cobalt residue are active.

Intrinsic factor was first noted in 1929. The lack of intrinsic factor was found to result in the development of pernicious anemia. The polypeptide is present in gastric secretions and facilitates the physiological uptake of vitamin B12. Intrinsic factor is of 55–60 k molecular weight, consisting of a single continuous peptide strand configured with a single B12 binding site. The material is recognized for its high specificity to only biologically active forms of B12. Upon binding B12, intrinsic factor undergoes a conformational change which accommodates binding to the intrinsic factor receptor; this conformational change is associated with an increase in affinity toward the intrinsic factor receptor.

A second B12 binding protein found in gastric secretions is R protein. R protein lacks the stringent specificity of intrinsic factor. Specifically, R-protein binds all corrin ring structures including cobamide, cobinamide and cobrinamide. R-protein has been identified as a contaminant of intrinsic factor preparations, and as such, can adversely impact the apparent specificity of said preparations.

Vitamin B12 assays were initially microbiologic. Later, after the specificity, affinity and stability of intrinsic factor was recognized, radioassays were developed which involved a competition reaction between radiolabelled vitamin B12 and vitamin B12 in a sample for binding to intrinsic factor.

Studies have shown that autoantibodies of certain patients directly block binding of vitamin B12 to intrinsic factor. Autoantibody fractions have been identified. Type I autoantibodies block vitamin B12 binding, hence, interfering with the function of intrinsic factor. Accordingly, it has been suggested that such autoimmune antibody be used to confirm the specificity of vitamin B12 binding activity in intrinsic factor preparations. P. A. Villanova, *National Committee For Laboratory Standards*, "Guidelines For Evaluating a B12 (Cobalamin) Assay" (1980).

Monoclonal antibodies have recently been described with specificity to intrinsic factor, but not for diagnostic purposes. Smolka and Donaldson, Gastroenterology 98: 607–614 (1990). Using human intrinsic factor, Smolka and Donaldson raised murine hybridomas, which were identified by dotblot analysis against immobilized intrinsic factor, followed by reselection for the ability to facilitate the immunoprecipitation of intrinsic factor-vitamin B12 complexes. They then recloned positive clones. Some of the positive clones secreted antibodies which bind to intrinsic factor-B12 complexes.

Pourfarzaneh et al. (WO 91/00519) describe immunoassays for vitamin B12 involving monoclonal antibodies said to be specific to the intrinsic factor:vitamin B12 complex and to the vitamin B12 binding site on intrinsic factor. Immunoassays using an antibody specific for the B12 binding site of intrinsic factor, such as the assays described in their application, require that the affinity and kinetics of the binding of the antibody to the B12 binding site be precisely balanced with the affinity and kinetics of the binding of B12 itself in order to obtain a assay of sufficient sensitivity. The kinetics of the interaction of B12 and intrinsic factor is slowed by the necessity of dissociating a particular antibody-intrinsic factor complex before B12 can bind to that intrinsic factor molecule and competitive assays of this type are slow and lack sensitivity.

Poufarzaneh et al also describe antibodies which are specific for the complex of intrinsic factor and vitamin B12. Such antibodies presumably are specific for epitopes which are made available by the conformational changes which occur in intrinsic factor upon B12 binding. Other researchers, as exemplified by Pfund et al., *Molec. Immunol.*, 27:495–502 (1990), have described the use of conformation sensitive antibodies to detect conformational changes in a protein, and to detect conformation sensitive antibodies. However, immunoassays in which an antibody is allowed to bind to an analyte and the extent to which it is subsequently released by later conformational changes in the analyte determined have not been described.

Sensitive, rapid assays for vitamin B12 are desirable. Most of the immunoassays now used require the use of radioisotopes and require the use of R-factor free intrinsic factor or the use of vitamin B12 analogues which bind to the R-factor to increase the sensitivity and specificity of the assays. Such radioassays are described by way of example in U.S. Pat. Nos. 4,188,189 and 4,426,455.

SUMMARY OF THE INVENTION

This invention involves the application of anti-intrinsic factor antibodies in rapid, sensitive immunoassays for the detection of vitamin B12. Clearly, specificity of the assay for active forms of cobalamin remains entirely confined to intrinsic factor. Thus, the reagents used in this invention offer an extremely flexible and specific means for determining vitamin B12 levels in samples.

Two classes of antibodies to intrinsic factor are described. Antibodies of one class bind to intrinsic factor competitively with vitamin B12. As used herein, the words "competitively, competitive, and compete" refer to the ability of either antibodies of this class and/or vitamin B12 to prevent the binding of the other to intrinsic factor. Antibodies of the second class bind only to the complex of intrinsic factor and vitamin B12. Each class recognizes epitopes unique to one conformation of intrinsic factor, either free of B12 or complexed with B12.

In one embodiment of the invention, an assay for vitamin B12 may include the step of measuring the relative binding to intrinsic factor of vitamin B12 and a known amount of anti-intrinsic factor antibodies of the competitive class. Such antibodies include those that are directly competitive with vitamin B12 and those that are indirectly competitive with vitamin B12 as described below. Those antibodies referred to herein as "directly competitive" are specific for the vitamin B12 binding site of intrinsic factor and therefore compete directly with B12 for binding to that site. In a liquid sample, the amount of vitamin B12 and the antibody bound to intrinsic factor and will eventually establish an equilibrium, based largely on the respective concentrations and affinities of each for intrinsic factor.

Other, and particularly preferred, competitive antibodies, include those that can be considered competitive with vitamin B12 in the "allosteric" sense, literally "other site". These antibodies can also be considered to be "indirectly" competitive, in that the antibody and B12 can not be tightly bound to intrinsic factor at the same time, although they do not bind to the same site. "Allosteric competitive" or "allosteric competition" will be used herein to identify the competitive anti-intrinsic factor antibodies which cannot be tightly bound to intrinsic factor at the same time vitamin B12 is bound to intrinsic factor but which do not bind to the vitamin B12 binding site.

These preferred allosteric competitive antibodies will bind to intrinsic factor only in the absence of vitamin B12, but bind at a site distinct from the vitamin B12 binding site. Such antibodies can be used in an assay to detect vitamin B12 in a sample. The allosteric competitive antibodies are able to bind to intrinsic factor in the absence of vitamin B12. Upon the addition of a sample, vitamin B12 contained therein will be free to bind to the intrinsic factor at the B12 binding site. The binding of vitamin B12 will lead to the prompt release of previously bound antibody, presumably due to the conformational change in the intrinsic factor that occurs upon the binding of vitamin B12. Alternatively, the allosteric competitive antibody and sample may be added to intrinsic factor without preincubation; the B12 contained in the sample would be more easily able to displace the antibody than in the case of the directly competitive antibodies because prior dissociation of the intrinsic factor from the antibody would not be required.

The kinetics, e.g., extent and rate, at which the previously bound allosteric competitive antibody is released from intrinsic factor in the presence of vitamin B12 can be determined and used, in turn, in any of a variety of ways, in order to determine the amount of vitamin B12 in a sample. Some methods include enzyme immunoassay, radioimmunoassay or chemiluminescent assay.

In addition to their applicability to the binding of vitamin B12 and intrinsic factor, allosteric competitive antibodies of the sort described in the present invention, appear to provide a particularly unique approach to any immunoassay that involves the binding of a first binding partner to a second binding partner to form a binding pair where one binding partner undergoes a conformational change when bound to the its binding partner. Such allosteric competitive antibodies can be used in any situation in which an antibody can be prepared that recognizes a conformational determinant of the first binding partner, in its unbound form, where that conformational determinant is altered upon the binding of the second binding partner, in such a way as to cause the release of the bound allosteric competitive antibody.

In another embodiment of the invention, an assay may be performed to stoichiometrically measure the vitamin B12/intrinsic factor complex formation. The unique hybridoma selection procedure described herein permits identification and differentiation of monoclonal antibodies which recognize structural, functional and conformational epitopes in the intrinsic factor molecule.

Basically, a method of the invention relates to an assay for vitamin B12 in which a sample suspected of containing vitamin B12 is complexed with intrinsic factor and an antibody which specifically binds to intrinsic factor competitively with vitamin B12 (in which case the antibody is present in a predetermined amount) or specifically binds to vitamin B12/intrinsic factor complexes, wherein either the intrinsic factor or the antibody to intrinsic factor is labeled and one of them is immobilized to a solid support. The general steps of immunoassays are well known in the art, and are applicable to the instant invention.

This invention also relates to diagnostic kits for assaying vitamin B12 in samples, comprising a predetermined amount of intrinsic factor and a predetermined amount of an antibody that specifically binds to intrinsic factor in an amount directly related to the presence or amount of vitamin B12 present in the sample, wherein either the intrinsic factor or antibody is directly or indirectly labeled with a signal-producing compound. The kit also preferably includes a solid support to which the intrinsic factor or antibody has been directly or indirectly bound.

This invention also relates to a method of obtaining monoclonal antibodies useful with the assay method of this invention and to the monoclonal antibody reagents.

BRIEF DESCRIPTION OF THE DRAWING

In the Drawing:
FIG. 1 is a graph of known B12 concentration against luminometer signal inhibition and useful in a method of the invention.

FIG. 2 is a graph showing a displacement curve showing the effect the addition of vitamin B12 has on precomplexed antibody and intrinsic factor as examined by surface plasmon resonance.

DETAILED DESCRIPTION OF THE INVENTION

This invention provides immunoassays for vitamin B12 and particularly immunoassays utilizing monoclonal antibodies to intrinsic factor and/or to intrinsic factor/vitamin B12 complexes.

Monospecific antibodies to intrinsic factor may also be used in the assays of the invention. Such antibodies may be generated by inoculating laboratory animals such as mice or rabbits with purified intrinsic factor (e.g. swine origin) using conventional techniques. Animals with demonstrable antibody to total intrinsic factor are bled, and serum immunoglobulin is purified thereof. The antibody is subjected to primary immunoaffinity chromatography against immobilized intrinsic factor. Bound antibody specific for intrinsic factor is eluted from the column using a suitable chaotrope and dialyzed against a suitable buffer to remove the chaotrope. The antibody is then applied to a vitamin B12 saturated intrinsic factor column. Antibody which elutes through the column is collected for use in preparation of conjugates or attachment to a solid phase.

Monoclonal antibodies useful with the assays of this invention are obtained by preparing hybridomas which secrete the same. The hybridomas are prepared by generally following the well known methods described by Milstein and Kohler in Nature, 256: 495–497 (1975), the teachings of which are herein incorporated by reference.

Monoclonal antibodies which bind to the vitamin B12 binding site of intrinsic factor (or otherwise become bound to intrinsic factor in a manner which prevents subsequent intrinsic factor-vitamin B12 complexing) may be obtained and identified using the following method. Mice are immunized with purified intrinsic factor and given a single intravenous booster injection of intrinsic factor two to five days before they are to be sacrificed. After sacrifice, the spleens are aseptically removed, and the splenocytes aseptically harvested using conventional techniques. Cell fusion with a plasmocytoma cell line is then carried out using well known methods. Appropriate cell lines are known in the art. Desirably, the cell line used with the method of this invention will secrete complete antibodies rather than fragments.

Following plating and several days growth in culture, the cell supernatants are screened using a suitable assay vessel (e.g. 96 well plate) sensitized with B12-free intrinsic factor. Half of the vessels are treated with a 10 ug/ml B12 solution, and washed. Duplicate samples of culture supernatant are then applied to both B12-free and B12 saturated vessels. Wells showing antibody binding in the absence of B12, and no binding in the presence of B12 are retained for use in competitive assays to compete with vitamin B12 in the sample for the binding site on intrinsic factor.

In a preferred embodiment, and particularly for the identification of allosteric competitive antibodies, before the cell supernatants containing antibody are screened, free vitamin B12 is extracted from each supernatant by contacting the supernatant with a material which will extract free vitamin B12 and other small molecular weight compounds from the sample but not monoclonal antibodies. The importance of removing free vitamin B12 will become clear to those skilled in the art. Antibodies that, by definition, will not be able to bind intrinsic factor or that will be released from binding, in the presence of vitamin B12 will be particularly difficult to detect if there are even trace amounts of vitamin B12 present. Dextran coated charcoal is particularly preferred in this method.

Monoclonal antibodies recognizing the intrinsic factor/B12 complex may be obtained using similar immunization techniques with a modified screening method. The cells again are screened using suitable assay vessels sensitized with vitamin B12-free intrinsic factor. Half of the vessels are saturated with B12, and washed. Duplicate samples of culture supernatant may be applied to both the B12-free and B12 saturated vessels. Wells showing elevated antibody binding in the presence of B12, and lower binding in the absence of B12 should be retained as candidates for use in the assays of the invention to directly bind to intrinsic factor/vitamin B12 complexes.

A particularly preferred allosteric competitive monoclonal antibody was obtained using the methods of this invention. A sample of the subject hybridoma was deposited at the American Type Culture Collection, 12301 Parklawn Drive, Rockville, Md. on Mar. 29, 1991, and has been assigned ATCC number ATCC-HB10711. The antibody produced by that hybridoma is referred to herein as 585.3A3A8.

Intrinsic factor useful as a reagent with this invention is preferably hog intrinsic factor, obtained by well known methods, although intrinsic factor obtained from any source may be used.

In one embodiment of the invention, a direct assay procedure may be used. In such an assay, intrinsic factor may be covalently or noncovalently attached to a solid phase support. Then the solid support with intrinsic factor attached is incubated with sample containing vitamin B12 for a sufficient period of time to allow the vitamin B12 present in the sample to bind to the intrinsic factor, and then is washed. A known (excess) amount of monospecific antibody or preferably, monoclonal antibody, which specifically binds to the intrinsic factor/vitamin B12 complex and which has been labelled with a detectable label using known techniques is incubated with the solid support for a sufficient period of time to allow the labelled antibody to bind to the bound intrinsic factor-B12 complex. The solid support is then washed and the amount of labelled antibody that is bound to the complex is determined. The amount of bound antibody is directly proportional to the amount of vitamin B12 in the sample.

In a preferred embodiment of the invention, monospecific or monoclonal antibody which specifically binds to intrinsic factor at the vitamin B12 binding site (or otherwise becomes bound to intrinsic factor in a manner which prevents subsequent intrinsic factor-vitamin B12 complexing) is covalently or noncovalently bound to a solid phase support. Then, sample containing vitamin B12 is combined with a known quantity of labelled intrinsic factor and incubated with the solid support for a sufficient period of time to allow binding to the immobilized antibody of any intrinsic factor that is not complexed with vitamin B12. The amount of bound or free labelled intrinsic factor is then determined using conventional means. Alternatively, intrinsic factor may be bound to the solid support and the monospecific or monoclonal antibody may be labelled and mixed with the sample. In this assay, the antibody and vitamin B12 compete for intrinsic factor binding sites; known protocols for immunoanalysis using competing reactions are employed.

In another preferred embodiment of the invention, involving the use of allosteric competitive antibodies, monospecific or monoclonal antibodies are employed that specifically bind to intrinsic factor in the absence of vitamin B12, and that are released from binding upon introduction and binding of vitamin B12. The amount of antibody released can be measured and correlated with the amount of vitamin B12 present in the sample, in any suitable manner within the skill of those in the art.

The monoclonal antibodies obtained using the methods of this invention can be used in connection with intrinsic factor in a wide variety of immunoassay formats such as sandwich assay formats, and the current invention is not limited to any specific formats or protocols.

"Solid phase support" as used herein refers to an insoluble material to which one component of the assay may be bound. Known materials of this type include hydrocarbon polymers such as polystyrene and polypropylene, glass, metals, and gels. Such supports may be in the form of beads, tubes, strips, disks and the like. Magnetic particles are particularly preferred for use with the assays of this invention.

"Labelled", "labelled conjugated" and the like refer to a conjugate of intrinsic factor, antibody or other binding reagent with a chemical label such as an enzyme, a fluorescent compound, a radioisotope, a chromophore, or any other detectable chemical specie, the conjugate retaining the capacity to specifically bind to its binding partner. "Detector," "label detector," "detection system," and the like, as exemplified below, refer to a chemical system that provides perceptible signals, commonly electromagnetic radiation or absorption of the same, leading to perceptible color changes, fluorescence, chemiluminescence and the like, when contacted with a specific enzyme or other label. When enzyme labels are used, the detection system desirably employs a substrate and a chromogen. Several convenient, known chromogens are available which produce visible color when added to their specific enzymes and substrates. For example, p-nitrophenolphosphate has been used for detecting alkaline phosphatase.

The invention may be better understood by reference to the following non-limiting examples.

EXAMPLE 1

Preparation of Antibodies

Eight week old female BALB/c mice were immunized on a biweekly basis with 10 ug/dose of porcine intrinsic factor in Incomplete Freund's adjuvant by the intraperitoneal route. The mice were sacrificed by cervical dislocation, and the spleens surgically removed. The spleens were transferred to a petri dish containing 5 ml of Dulbecco's modified medium (DME) containing 100 ug/ml gentamycin. The splenocytes were freed by teasing the tissue apart. The splenoctyes were washed once with DME, and combined in a 5:1 ratio with washed SP2/O cells, from a plasmocytoma cell line that can be obtained commercially.

The cells were pelleted, excess supernatant removed, and the cells resuspended in 1 ml of buffered 50% polyethylene glycol solution (Boehringer Mannheim). The cells were incubated at room temperature for 120 seconds prior to centrifugation at approximately 400×g for 6 minutes. Fused cells were then centrifuged, gently rinsed with DME, resuspended in Iscove's Modified DME with SP2/0 conditioned medium and gently transferred to 75 cm² flask.

Following an overnight incubation at 37° C. in $CO_2$, the cells were diluted to $2 \times 10^6$ cells/ml in conditioned medium, and seeded into 96 well plates (250 ul/well). After 7–10 days, the supernatants were screened as follows. 96 well flatbottom polystyrene plates (Immulon I, from Dynatech) were presensitized overnight with porcine intrinsic factor (obtained from BiosPacific, Inc., 1 ug/ml in 50 mM phosphate buffered saline (PBS), pH 7.2), 100 ul/well. The plates were washed, and then blocked with 1% bovine serum albumin (BSA) in 50 mM phosphate buffered saline, pH 7.2 for 30 minutes. After washing to remove excess BSA, the intrinsic factor in half the wells was complexed by preincubation with 100 ul of a 10 ug/ml B12 solution.

200 ul of each culture supernatant were transferred into microtiter plates. Each well was then mixed with 50 ul of dextran-coated charcoal slurry (150 mg dextran and 1.5 gm Norit A in 100 ml, 150 mM PBS) at ph 7.4 and stirred overnight at 40° C. Following a 5 minute incubation, the charcoal was sedimented by centrifugation.

Culture supernatants were then transferred in parallel to wells containing intrinsic factor and intrinsic factor-B12 complex. Polyclonal mouse anti-intrinsic factor and normal mouse serum served as positive and negative controls, respectively. Following a 30 minute incubation, the plates were washed, and peroxidase-labelled goat anti-mouse antibody (commercially available, obtained from Calbiochem, Inc.) was added to all wells of the plate. The plates were thoroughly rinsed, and ABTS substrate (Peroxidase Substrate from Kirkegaard and Perry Laboratories, Inc.) was added. The reactivity of the cells in the wells was measured spectrophotometrically as a ratio of absorbances at 410 nm and 450 nm. Several wells were identified with cells having reactivity in the absence of B12 and no detectable reactivity with B12 using the charcoal screening method described above. These cells were subcultured for further examination (e.g., +B12/−B12 absorbance ratios of 0.02/0.2).

Hybridoma cells were identified in other wells which exhibited enhanced binding in the presence of B12 (e.g., +B12/−B12 absorbance ratios of 0.7/0.15).

EXAMPLE 2

Preparation of Enzyme Labelled Antibodies

Maleimide groups were introduced onto alkaline phosphatase (ALP) by reaction with a 30-fold molar excess of sulfosuccinimidyl 4-(N-maleimidomethyl)cyclohexane1-carboxylate in 0.2 M imidazole, pH 9.0; excess reagent was removed by gel filtration on a 1×28 cm column of Sephadex G-50 in PBS. Thiols were introduced onto the antibody (obtained through the procedure described in Example 1) with 40 mM N-acetyl homocysteine thiolactone in 0.1M sodium bicarbonate, 0.15 M NaCl, 1 mM EDTA, pH 8.0; excess reagent was removed on a second gel filtration column in the PBS+1 mM EDTA. Conjugation was achieved by incubating modified enzyme with modified antibody at a 2:1 molar ratio of ALP to antibody for two hours at room temperature. The conjugate was purified by size exclusion chromatography on Sephacryl S-300 (1.5×120 cm) in Tris-buffered saline, pH 8.0.

EXAMPLE 3

Preparation of Enzyme Labelled Intrinsic Factor

Maleimide groups were introduced onto alkaline phosphatase as above. Purified intrinsic factor (obtained from Scripps Laboratories, Inc.) was reacted with 40 mM N-acetyl homocysteine thiolactone in 0.08 M sodium bicarbonate, 0.12 M NaCl, 8 mM EDTA, pH 8.0; excess reagent was removed on a second gel filtration column in the PBS+1 mM EDTA, as above. Conjugation was achieved by incubating modified intrinsic factor with a two- to-three-fold molar excess of modified enzyme for two hours at room temperature. Under these conditions thiols, such as were introduced into intrinsic factor, are known to react stoichiometrically with maleimides, as on the modified enzyme, to form chemically stable linkages. The conjugate was purified by size exclusion chromatography on Sephacryl S-300 1.5×120 cm) in Tris-buffered saline, pH 8.0.

EXAMPLE 4

Preparation of Vitamin B12 Conjugate

Cyanocobalamin-d-carboxylic acid was coupled to alkaline phosphatase through a mixed anhydride with isobutyl chloroformate. 1 mg of the cobalamin derivative was dissolved in 250 ul dimethylformamide and incubated with 2 ul triethylamine and 1 ul isobutyl chloroformate on ice for 30 min. 100 ul of this reaction mixture was added to 2 mg alkaline phosphatase in 900 ul 0.05 M bicarbonate, 0.15 M NaCl, 1 mM MgC12, pH 9.0, and incubated at room temperature for 2 hours. Excess reagents were removed by dialysis against charcoal suspended in 50 mM Tris, 0.15 M NaCl, 1 mM MgC12, 0.1 mM ZnC12, pH 7.4, and gel filtration on a column of Sephadex G-50 (1.5×28 cm) in the same buffer. The resulting conjugate contained 7.3 moles cobalamin per mol enzyme.

EXAMPLE 5

Preparation of Solid Phase

Purified monoclonal allosteric competitive antibody 585.3A3A8 was bound to goat anti-mouse (obtained from commercial sources) sensitized magnetic particles (Advanced Magnetics, Inc., cat. # 4340D) at the level of 10 ug/100 ul of 1 mg/ml particle suspension stock. Antibody was adsorbed for 1 hr. in suspension. Afterward, the particles were sedimented in a magnetic field, washed twice with 10 mM Tris containing 5 uM KCN, pH 8.0, and resuspended in 10 mM Tris containing 5 uM KCN, pH 8.0.

EXAMPLE 6

Competitive Assay for Vitamin B12

In setting up the assay, 200 ul of B12 containing samples or standards in 10 mM Tris containing 5 uM KCN, pH 8.0 were transferred to 10×60 mm borosilicate glass test tubes. To each reaction tube was added 100 ul (0.1 ug) of intrinsic factor-alkaline phosphatase conjugate of a 1:1 molar ratio. The reactants were incubated for 15 minutes at 37° C. in a shaker water bath agitating at approximately 60 rpm. 50 ul of particles (with bound allosteric competitive antibody, prepared as described in Example 5) were added to the reaction mixture, and incubated at 37° C. with agitation for an additional 30 minute time span. The reaction was stopped by sedimentation for 2 minutes in a magnetic field. The tubes were rinsed twice with 1 ml of 50 mM Tris, 0.15 M NaCl, 0.1% Triton X-100, pH 7.4. 200 ul of Lumiphosä 530 (Registered trademark of Lumigen, Inc. Detroit, Mich.) was added to each tube, and the reaction initiated by static incubation at 37° C. for 5 minutes. The tubes were then cooled to room temperature for 2 minutes, and then analyzed on a Ciba-Corning Berthold Luminometer within 5 minutes. The resulting signal inhibition was plotted as an arithmetic function of B12 concentration, as shown in FIG. 1.

Serum or plasma samples containing unknown amounts of vitamin B12 are pretreated to release B12 from endogenous B12 binding proteins by, for example, incubating at high pH in the presence of KCN to stabilize the vitamin. The supernatant fluids from these pretreated samples are assayed by the same protocol as the standards above and the concentration of vitamin B12 determined by comparison of the luminometer signal with a standard curve such as FIG. 1.

It can be seen in FIG. 1 that as vitamin B12 levels in the sample increased relative luminescence units (RLU's) decreased. This occurrence supports the conclusion that vitamin B12 in the sample prevented binding of allosteric competitive antibody to intrinsic factor.

EXAMPLE 7

Direct Assay for Vitamin B12

Vitamin B12 in samples can be determined in a direct assay using an antibody which binds to the intrinsic factor: B12 complex, such as the monoclonal antibody identified as 587.5A3. Particles sensitized with this antibody in accordance with the methods of Example 5 may be added to a B12-intrinsic factor reaction mixture as described for 585.3A3A8 with the exception that higher levels of intrinsic factor-alkaline phosphatase conjugate would be used (e.g., 10 ug). The subsequent reaction steps are executed as described in Example 6. The resulting signal increases are plotted as a function of B12 levels.

EXAMPLE 8

Dissociation of Intrinsic Factor From Antibody by B12

The dissociation of intrinsic factor from the allosteric competitive antibody of the invention was examined by surface plasmon resonance using a biosensor instrument ("BIAcore", Pharmacia). Surface plasmon resonance is useful for measuring changes in mass that occur on the surface of a test substrate as the result of immunoassay binding reactions. Such changes in mass correlate with changes in optical properties that can be detected and electronically read using the biosensor.

Specifically, analysis of the interactions of intrinsic factor, vitamin B12 and anti-intrinsic factor monoclonal antibody 585.3A3A8 were performed on a BIAcore instrument (Pharmacia Biosensor AB, Uppsala, Sweden). Using this instrument interactions between nanogram quantities of proteins can be measured by the changes such interactions cause in the above-described phenomenon known as surface plasmon resonance ("SPR"). The changes in SPR signal can be monitored in real time, and subsequent calculations based on the real-time data permit determinations of kinetic and affinity parameters associated with the interacting molecules.

In SPR the protein interactions occur in aqueous buffer with a 100 nm thick layer of linear dextran that is attached to a gold film on the surface of a glass slide. Near infrared light is focused down the length of the glass slide at a small angle with respect to the plane of the gold-glass interface. The light impinges on the gold-glass interface and is reflected. Because of the presence of a cloud of free electrons (a plasmon) in the metal, as the light is reflected some of its energy penetrates the interface and is absorbed. The amount of absorbed energy and the precise angle at which maximum absorbance occurs are dependent on the refractive index of the material on the other (aqueous) side of the interface. That refractive index is in turn dependent on the mass of material present in the first few hundred nanometers on that side of the interface. As the accumulated mass changes (e.g., through binding of a protein to the surface), the SPR signal changes and the instrument translates the signal into data quantitatively related to the amount of mass accumulated. The data are quantified in arbitrary (but fixed, once defined) "resonance units", or "RU".

For the investigation of the interaction between MAB 585.3A3A8 and intrinsic factor, rabbit antibody against mouse IgG was covalently attached (immobilized) to the dextran surface. The monoclonal antibody was captured onto the surface by the rabbit antibody, then intrinsic factor (Scripps 11024) was captured by the antibody. The dissociation rates of intrinsic factor from the surface in the presence and absence of B12 (Sigma Chemical Co. Cat. No. V2876) were determined. In particular, the following methods were used, and all methods were performed at 25 degrees C.

A. Installation of Biosensor Surface.

System buffer, HEPES buffered saline ("HBS"), was prepared as 10 mM "HEPES" (N-[2-hydroxyethyl]piperazine-N'-[2-ethanesulfonic acid, Sigma Catalog No. H 3375), 150 mM NaCl, 3.4 mM EDTA, and 0.05% surfactant ("P 20", Pharmacia Biosensor catalog # BR-1000-54), and made to pH 7.4 with 5M NaOH, filtered and degassed.

A biosensor chip "CM5" (Pharmacia Biosensor catalog # BR-1000-12, dextran/gold/glass surface) was installed in the instrument and the system flushed with HBS.

The signal for a newly installed chip was normalized with 40% glycerol as described in the instrument operating manual. The resonance trough in each of the four flow cells bottomed out at near 8000 RU between pixels 13 and 14.

B. Immobilization of Rabbit Anti-Mouse IgG.

Reagents in the amine coupling kit (Pharmacia Biosensor catalog # BR-1000-50) were made up according to the manufacturer's instructions and stored frozen until use.

The carboxylic acid groups of the dextran surface of chip CM5 were activated with a solution of "EDC" and "NHS". Immediately after activation, a solution of rabbit anti-mouse IgG1 ("RxM", Pharmacia Biosensor catalog # BR-1000-55) at 100 micrograms/ml in 10 mM sodium acetate, pH 5.0 was injected for 6 minutes. Activated groups not reacting with protein were capped with an injection of ethanolamine.

The newly immobilized RxM surface was conditioned by three cycles of a six minute injection of mouse IgG1 (Sigma Chemical Co. Cat. No. M7894) at 50 micrograms/ml in HBS followed by regeneration of the surface with a two minute injection of 1.0 M formic acid.

The RxM immobilization increased the baseline signal by about 10,000 RU, and this amount of RxM captured about 3000 RU of mouse IgG1 under the conditions of the conditioning cycles.

C. Experiments on the RxM Surface.

For experiments on the RxM surface, monoclonal antibody diluted in HBS was injected to be captured by the RxM. For most experiments about 1500 RU of antibody was captured. Intrinsic factor diluted in HBS was then injected to be captured by the monoclonal antibody. Usually, about 600 RU of intrinsic factor was captured. The decay of the intrinsic factor signal was then followed and rate constants calculated based on a model of first order exponential decay. The off rates were observed in buffers HBS, HBS containing 5 micromolar KCN ("HBS/KCN"), and HBS/KCN containing 5, 10, 20, and 50 micromolar B12. At the end of each cycle the surface was regenerated with 1.0 M formic acid.

FIG. 2 shows a real time plot of the dissociation of IF from antibody. The portion of the plot representing the first 100 seconds represents the spontaneous dissociation of IF in buffer. The spikes in the plot that are apparent at approximately 100 seconds correlate with the onset of dissociation conditions brought about by the addition of control and B12-containing KCN buffer. The lines of the plot appear in pairs that relate to the duplicate samples. From top to bottom, the pairs represent, respectively, the addition of 0, 5, 10, 20, and 50 micromolar B12 in buffer.

The results shown in FIG. 2 exhibit a first order dissociation rate of the antibody-intrinsic factor complex. The rate was increased by the addition of vitamin B12 in a degree directly dependent on the concentration of B12. This increase in dissociation rate would not be possible if the antibody itself were bound to the B12 binding site of intrinsic factor, since the antibody-intrinsic factor complex would have to first dissociate at its spontaneous dissociation rate prior to B12 binding. The fact that B12 can affect the dissociation of precomplexed antibody-intrinsic factor is instead interpreted as meaning that B12 is able to bind to intrinsic factor complexed to antibody. The antibody and B12 therefore do not bind to the same site, yet the addition of B12 causes the dissociation of previously bound antibody.

While a preferred embodiment of the present invention has been described, it should be understood that various changes, adaptations and modifications may be made therein without departing from the spirit of the invention and the scope of the appended claims.

What is claimed is:

1. A monoclonal antibody that specifically binds to intrinsic factor only in the absence of vitamin B12 and exhibits an increase in the first order dissociation rate of the antibody-intrinsic factor complex in the presence of vitamin B12, wherein the dissociation rate is dependent on the concentration of vitamin B12.

2. A kit for determining the presence of vitamin B12 in a sample, the kit comprising intrinsic factor and a labelled monoclonal antibody, the antibody being one which will specifically bind to the intrinsic factor only in the absence of vitamin B12 and will exhibit an increase in the first order dissociation rate of the antibody-intrinsic factor complex in the presence of vitamin B12, wherein the dissociation rate is dependent on the concentration of vitamin B12.

3. The kit of claim 2 further comprising a second antibody which will specifically bind to intrinsic factor without regard to the presence or absence of vitamin B12.

4. The kit of claim 3 wherein the second antibody is bound to a solid phase support.

5. A kit for assaying for vitamin B12 in a sample comprising (a) a solid phase support to which is bound a predetermined amount of a monoclonal antibody that is capable of specifically binding to intrinsic factor only in the absence of vitamin B12 and exhibits an increase in the first order dissociation rate of the antibody-intrinsic factor complex in the presence of vitamin B12, wherein the dissociation rate is dependent on the concentration of vitamin B12, and (b) a predetermined amount of a labelled intrinsic factor.

6. The kit of claim 5 wherein the label is alkaline phosphatase and further comprising a substrate to detect the presence or amount of the label.

7. A method of obtaining a monoclonal antibody that binds to intrinsic factor only in the absence of vitamin B12, and exhibiting an increase in the first order dissociation rate of the antibody-intrinsic factor complex in the presence of vitamin B12, wherein the dissociation rate is dependent on the concentration of vitamin B12, comprising the steps of:
  a) immunizing an animal with substantially purified intrinsic factor;
  b) isolating splenic lymphocytes from the immunized animal;
  c) fusing the isolated splenic lymphocytes with a plasmocytoma cell line to obtain a plurality of hybridoma clones which secrete antibody;
  d) extracting free vitamin B12 from a predetermined amount of culture supernatant containing antibody from each hybridoma clone;
  e) contacting a first sample of each extracted antibody-containing supernatant with intrinsic factor in the presence of vitamin B12;
  f) contacting a second sample of each extracted antibody-containing supernatant with intrinsic factor in the absence of vitamin B12;
  g) contacting an enzyme labelled antibody which specifically binds to immunoglobulin with each of the first and second samples;
  h) detecting the presence of labelled antibody present in each of the first and second samples; and
  i) isolating the hybridomas which secrete antibodies which bind to intrinsic factor only in the absence of vitamin B12 and exhibit an increase in the first order dissociation rate of the antibody-intrinsic factor complex in the presence of vitamin B12, wherein the dissociation rate is dependent on the concentration of vitamin B12.

8. The method of claim 7, wherein the extraction step (d) is performed using dextran coated charcoal.

9. A diagnostic assay method for determining the amount of vitamin B12 in a liquid sample comprising:
   (a) contacting the sample with a known amount of labeled intrinsic factor and a known amount of a monoclonal antibody bound to a solid phase, wherein the antibody specifically binds to intrinsic factor at a site on intrinsic factor that is distinct from the site on intrinsic factor to which vitamin B12 binds and which binds to intrinsic factor only in the absence of vitamin B12, and that exhibits an increase in the first order dissociation rate of the antibody-intrinsic factor complex in the presence of vitamin B12, said dissociation rate being dependent on the concentration of vitamin B12, wherein the intrinsic factor will specifically bind to vitamin B12 in the sample to form a vitamin B12-intrinsic factor complex;
   (b) separating the vitamin B12-intrinsic factor complex from the monoclonal antibody bound to the solid phase; and
   (c) determining the amount of vitamin B12 by measuring the amount of label associated with the vitamin B12-intrinsic factor complex or the amount of label bound to the antibody on the solid phase.

\* \* \* \* \*